United States Patent
Peichel et al.

(10) Patent No.: US 12,138,442 B2
(45) Date of Patent: Nov. 12, 2024

(54) EXTERNAL WIRELESS POWER TRANSFER COIL

(71) Applicant: Medtronic, Inc., Minneapolis, MN (US)

(72) Inventors: David J. Peichel, Minneapolis, MN (US); Ramesh Raghupathy, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 803 days.

(21) Appl. No.: 17/246,763

(22) Filed: May 3, 2021

(65) Prior Publication Data

US 2021/0346682 A1 Nov. 11, 2021

Related U.S. Application Data

(60) Provisional application No. 63/022,728, filed on May 11, 2020.

(51) Int. Cl.
*A61M 60/90* (2021.01)
*A61M 60/875* (2021.01)
*H02J 7/02* (2016.01)
*H02J 50/00* (2016.01)
(Continued)

(52) U.S. Cl.
CPC .......... *A61M 60/875* (2021.01); *A61M 60/90* (2021.01); *H02J 7/02* (2013.01); *H02J 50/005* (2020.01); *H02J 50/10* (2016.02); *H02J 50/90* (2016.02); *A61M 2205/3368* (2013.01);
(Continued)

(58) Field of Classification Search
CPC .............. A61B 2560/0219; A61M 2205/3368; A61M 2205/3633; A61M 2205/8243; A61M 2209/088; A61M 60/178; A61M 60/216; A61M 60/873; A61M 60/875; A61M 60/90; H01F 27/025; H01F 27/22; H01F 38/14; H02J 2310/23; H02J 50/005; H02J 50/10; H02J 50/90; H02J 7/02; H04B 5/79
See application file for complete search history.

(56) References Cited

U.S. PATENT DOCUMENTS

| 7,997,854 B2 | 8/2011 | LaRose et al. |
| 8,419,609 B2 | 4/2013 | Shambaugh, Jr. et al. |
| 8,620,447 B2 | 12/2013 | D'Ambrosio et al. |

(Continued)

FOREIGN PATENT DOCUMENTS

CN 109586365 A 4/2019

OTHER PUBLICATIONS

Cool Polymers®, Inc., CoolPoly® D8102 Thermally Conductive Thermoplastic Elastomer (TPE), Rev. Jun. 30, 2009, 1 page.
(Continued)

*Primary Examiner* — George Manuel
(74) *Attorney, Agent, or Firm* — Shumaker & Sieffert, P.A.

(57) ABSTRACT

An external coil system for a transcutaneous energy transfer system (TETS), the external coil being configured to transfer energy sufficient to power and implantable blood pump. The system includes a housing containing the external coil, the housing includes a thermal insulating base, the external coil being partially disposed within the thermal insulating base and a thermally conductive plastic, the external coil being partially disposed within the thermally conductive plastic.

20 Claims, 3 Drawing Sheets

(51) Int. Cl.
 *H02J 50/10* (2016.01)
 *H02J 50/90* (2016.01)
(52) U.S. Cl.
 CPC .............. *A61M 2205/3633* (2013.01); *A61M 2205/8243* (2013.01); *A61M 2209/088* (2013.01)

(56) References Cited

U.S. PATENT DOCUMENTS

| | | |
|---|---|---|
| 10,143,788 B2 | 12/2018 | Rudser et al. |
| 2011/0021863 A1* | 1/2011 | Burnett .................. A61N 2/006 600/13 |
| 2013/0310629 A1 | 11/2013 | Lafontaine |
| 2015/0283313 A1 | 10/2015 | Huber |
| 2015/0290379 A1 | 10/2015 | Rudser et al. |
| 2017/0216508 A1 | 8/2017 | Zilbershlag et al. |
| 2019/0076587 A1 | 3/2019 | Rudser et al. |
| 2019/0207425 A1 | 7/2019 | Hansen |
| 2019/0314564 A1 | 10/2019 | Rudser et al. |
| 2020/0078596 A1 | 3/2020 | Holinski et al. |

OTHER PUBLICATIONS

International Search Report and Written Opinion dated Aug. 4, 2021, for corresponding International Application No. PCT/US2021/030811 International Filing Date: May 5, 2021 consisting of 22-pages.

\* cited by examiner

EXTERNAL WIRELESS POWER TRANSFER COIL

CROSS-REFERENCE TO RELATED APPLICATION

This application claims the benefit of U.S. Application Ser. No. 63/022,728, filed May 11, 2020.

FIELD

The present technology is generally related to external power transfer coils and a system for the same.

BACKGROUND

Transcutaneous energy transfer systems (TETS) include an external coil coupled to a battery, which transfers power through the skin of the patient toward an aligned internal coil implanted within the patient, which is coupled to a medical device requiring power. Such an arrangement avoids certain adverse events, such as infection, that occur in percutaneous systems in which a power cable or driveline is inserted through the skin to transfer power to the medical device. However, when the external coil and the internal coil are misaligned, power transfer between the coils becomes less efficient and more heat will be emitted from the external coil.

SUMMARY

The techniques of this disclosure generally relate to external power transfer coils and a system for the same.

In one aspect, the present disclosure provides an external coil system for a transcutaneous energy transfer system (TETS), the external coil being configured to transfer energy sufficient to power and implantable blood pump. The system includes a housing containing the external coil, the housing includes a thermal insulating base, the external coil being partially disposed within the thermal insulating base and a thermally conductive plastic, the external coil being partially disposed within the thermally conductive plastic.

In another aspect of this embodiment, the external coil is sandwiched between the thermal insulating base and the thermally conductive plastic.

In another aspect of this embodiment, the external coil is enclosed within the thermal insulating base and the thermally conductive plastic.

In another aspect of this embodiment, the thermal insulating base defines a first channel and the thermally conductive plastic defines a second channel, and wherein the external coil is sized to be received within the first channel and the second channel when sandwiched between the thermal insulating base and the thermally conductive plastic.

In another aspect of this embodiment, the first channel is deeper than the second channel.

In another aspect of this embodiment, the thermal insulating base is coated with rubber.

In another aspect of this embodiment, the system further includes at least one temperature sensor disposed between the external coil and the thermally conductive plastic.

In another aspect of this embodiment, the thermal insulating base is composed of foam.

In another aspect of this embodiment, the system further includes a garment alignment fabric layer coupled to the housing.

In another aspect of this embodiment, the garment alignment fabric layer is composed of polypropylene.

In another embodiment, an external coil system for a transcutaneous energy transfer system (TETS), the external coil being configured to transfer energy sufficient to power and implantable blood pump. The system includes a housing containing the external coil, the housing includes a foam base, the external coil being partially disposed within the foam. A thermally conductive plastic is included within the housing, the external coil being partially disposed within the thermally conductive plastic, the thermally conductive plastic being coated with rubber. A plurality of temperature sensors is disposed within the housing.

In another aspect of this embodiment, the external coil is sandwiched between the foam base and the thermally conductive plastic.

In another aspect of this embodiment, the external coil is enclosed within the foam base and the thermally conductive plastic.

In another aspect of this embodiment, the foam base defines a first channel and the thermally conductive plastic defines a second channel, and wherein the external coil is sized to be received within the first channel and the second channel when sandwiched between the foam base and the thermally conductive plastic.

In another aspect of this embodiment, the first channel is deeper than the second channel.

In another aspect of this embodiment, the thermal insulating base is coated with rubber.

In another aspect of this embodiment, the system further includes at least one temperature sensor disposed between the external coil and the thermally conductive plastic.

In another aspect of this embodiment, the system further includes a garment alignment fabric layer coupled to the base, the garment alignment fabric layer being configured to couple the housing to a garment.

In another aspect of this embodiment, the garment alignment fabric layer is composed of polypropylene.

In another embodiment, an external coil system for a transcutaneous energy transfer system (TETS), the external coil being configured to transfer energy sufficient to power and implantable blood pump. The system includes a housing enclosing the external coil, the housing includes a foam base coated with rubber and defining a first channel. A thermally conductive plastic defines a second channel, the external coil is sized to be received within the first channel and the second channel when sandwiched between the foam base and the thermally conductive plastic. A plurality of temperature sensors is disposed within the housing on the surface of the external coil. A garment alignment fabric layer is coupled to the housing.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
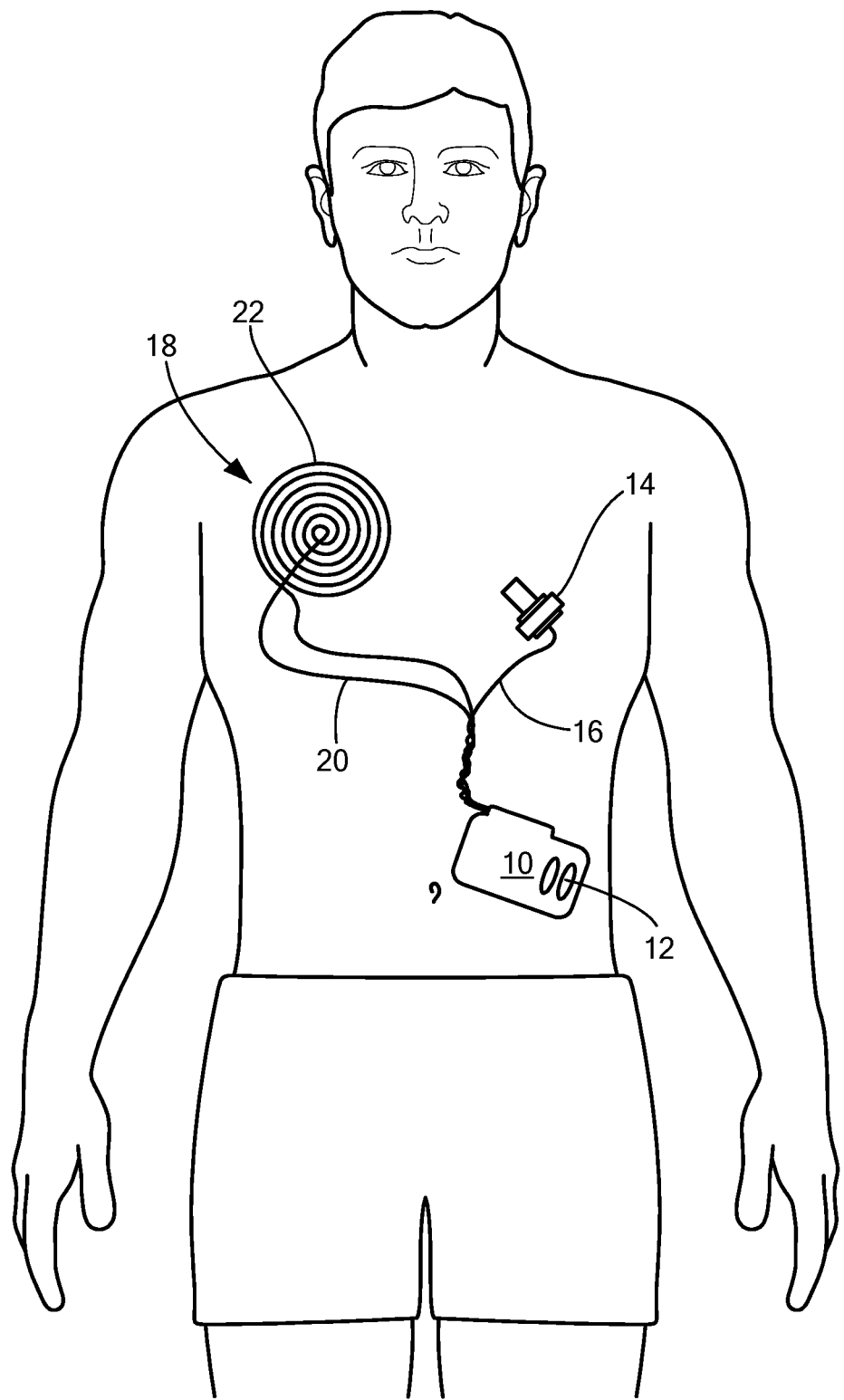
FIG. 1 is a an inside schematic view of fully implantable blood pump constructed in accordance with the principles of the present application.

Referring to the drawings in which like reference designators refer to like elements, there is shown in FIG. 1 an exemplary implantable controller for an implantable medical device constructed in accordance with the principles of the present application and designated generally as "10." The controller 10 may include one or more batteries 12 configured to power the components of the controller and provide power one or more implantable medical device, for example, a blood pump such as ventricular assist device (VAD) 14 implanted within the left ventricle of the patient's heart. VADs 14 may include centrifugal pumps, axial pumps, or other kinds electromagnetic pumps configured to pump blood from the heart to blood vessels to circulate around the body. One such centrifugal pump is the HVAD sold by HeartWare, Inc. and is shown and described in U.S. Pat. No. 7,997,854 the entirety of which is incorporated by reference. One such axial pump is the MVAD sold by HeartWare, Inc. and is shown and described in U.S. Pat. No. 8,419,609 the entirety of which is incorporated herein by reference. In an exemplary configuration, the VAD 14 is electrically coupled to the controller 10 by one or more implanted conductors that form a driveline 16 configured to provide power to the VAD 14, relay one or more measured feedback signals from the VAD 14, and/or provide operating instructions to the VAD 14. The controller 10 may include processing circuitry having one or more processors configured to operate the VAD 14 and to processes various signals received from the VAD 14.

Figure 2:
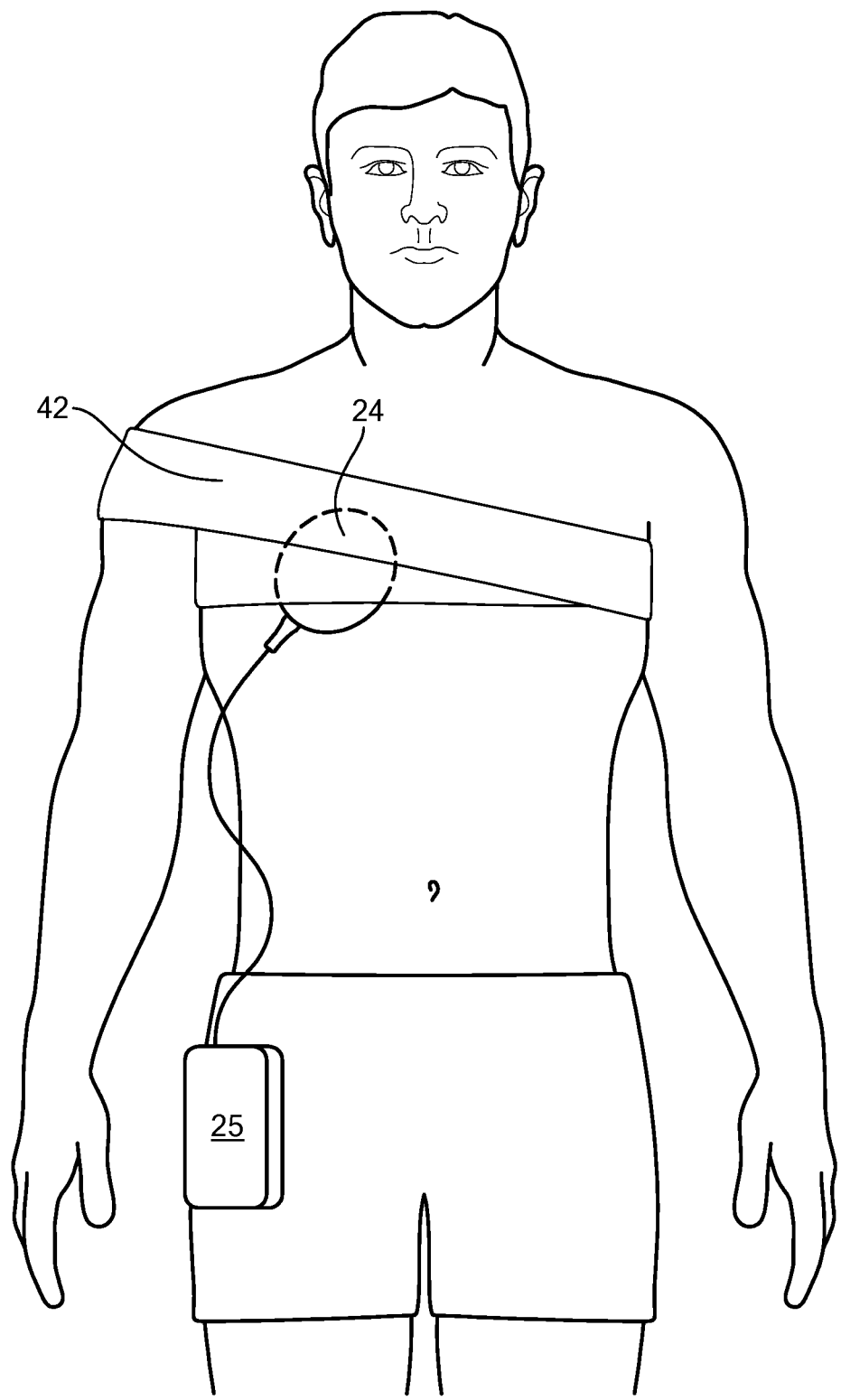
FIG. 2 is an external view of a controller/power supply and an external coil for power transfer to the implantable blood pump shown in FIG. 1.
Figure 3:
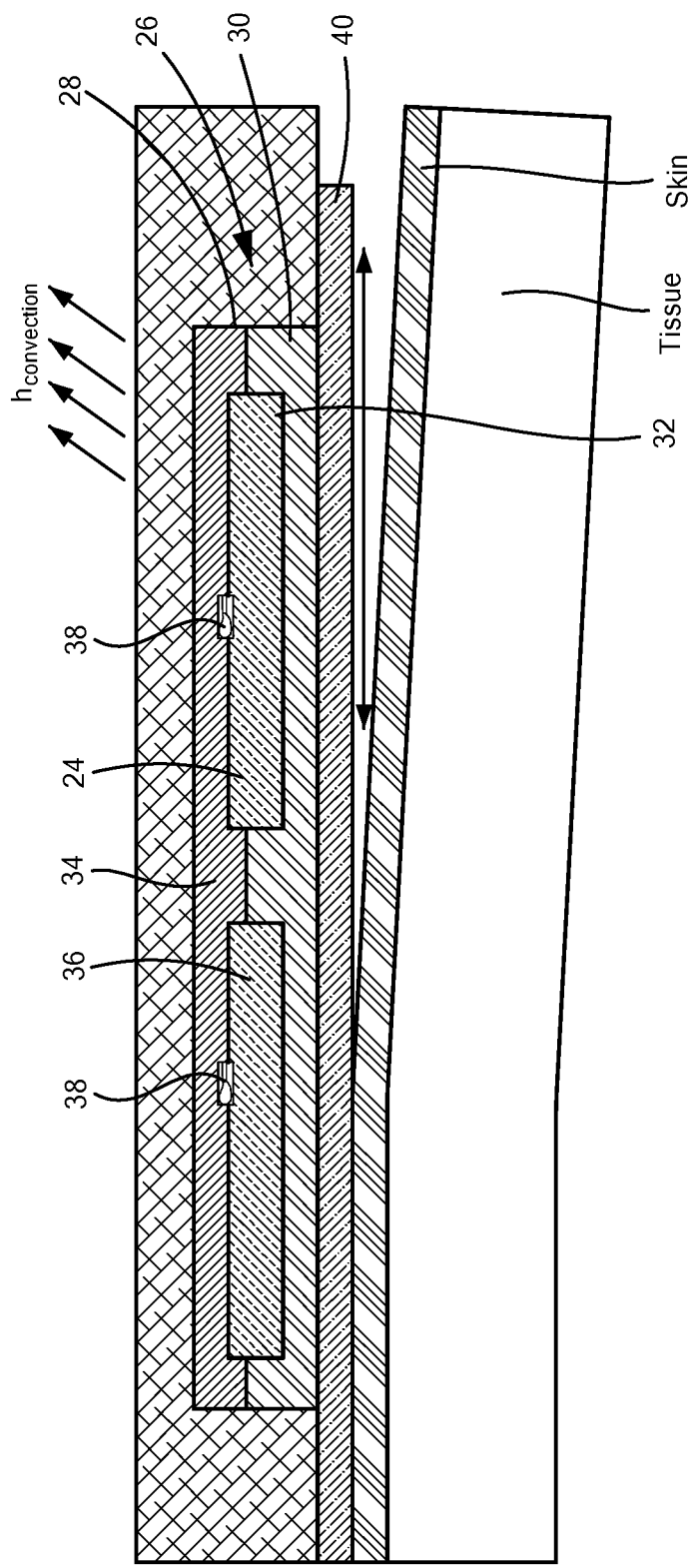
FIG. 3 is a side cross-sectional view of the external coil shown in FIG. 2.

Referring now to FIGS. 1-3, a receiving coil 18 may also be coupled to the controller 10 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission coil (not shown) coupled to an external battery and controller (not shown) disposed opposite the receiving coil 18 on the outside of the patient's body. The receiving coil 18 may be disposed within a hermetically or non-hermetically sealed package 22 that does not interfere with magnetic coupling of the receiving coil 18. An external or transmitting coil 24 may be positioned external to the patient, opposite the receiving coil 18, to transfer energy transcutaneous to the receiving coil 18. The external coil 24 may be composed of copper and is coupled to a power source such as a battery 25 and is configured to transfer power sufficient to power and operate the VAD 14. The external coil 24 may be part of a system or package 26 which houses the external coil 24. For example, as shown in FIG. 3, the external coil 24 is disposed and retained within a housing 28. The housing 28 includes a thermal insulating base 30, the external coil 24 being partially disposed within the thermal insulating base 30. The base 30 may be composed of a foam, for example, ethylene-vinyl acetate, or other closed cell foams or thermal insulators, and is configured to house a portion of the external coil 24. In particular, the base 30 may define a first channel 32 sized and configured to receive the external coil 24. The first channel 32 defines a depth such that when the external coil 24 is received within the first channel 32, a portion of the external coil 24 extends outward from the first channel 32. In the configuration shown in FIG. 2, the base 30 partially encloses the external coil 24 by extending around the sides of the external coil 24. In one configuration, the base is coated with a rubber, such as Santoprene.

Continuing to refer to FIG. 3, the housing 28 further includes a thermally conductive plastic 34, such as a thermoplastic elastomer, disposed opposite the base 30. The thermally conductive plastic 34 is configured to transfer heat from the external coil 24 out through a patient's clothing toward the ambient environment. In one configuration, the thermally conductive plastic 34 is composed of polypropylene, but any plastic that dissipates heat is contemplated. The thermally conductive plastic 34 operates as a lid and is positioned on the base 30 to create an enclosed space for the external coil 24. In particular, the thermally conductive plastic 34 and the base 30 cooperate to sandwich the external coil 24 therebetween such that the external coil 24 is completely concealed and enclosed within the housing 24. In one configuration, the thermally conductive plastic 34 defines a second channel 36 opposite the first channel 32. The second channel 36 may be the same depth or shallower than the first channel 32 and is sized to house the portion of the external coil 24 not disposed within the first channel 32. When the thermally conductive plastic 34 and the base 30 are pressed against each other the first channel 32 and the second channel 36 enclose and sandwich the external coil 24 within the housing 28.

Continuing to refer to FIG. 3, disposed between the thermally conductive plastic 34 and the external coil 24 may be one or more temperature sensors 38 configured to detect if the temperature of the external coil 24 rises above a predetermined temperature threshold. In one, the one or more temperature sensors includes two temperature sensors 38 coupled to the surface of the external coil 24. A garment alignment fabric layer 40 may also be included as part of the system 26 and coupled to the housing 28. The fabric layer 40 is configured to engage the housing 28 to align the housing 28 with the skin such that energy transfer occurs between the external coil 24 and the receiving coil 20. In one configuration, the fabric layer 40 is composed of polypropylene.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An external coil system for a transcutaneous energy transfer system (TETS), the system comprising:
 an external coil configured to transfer energy sufficient to power an implantable blood pump; and
 a housing comprising:
  a thermal insulating base, the external coil being partially disposed within and contacting the thermal insulating base; and
  a thermally conductive plastic, the external coil being partially disposed within and contacting the thermally conductive plastic.

2. The system of claim 1, wherein the external coil is sandwiched between the thermal insulating base and the thermally conductive plastic.

3. The system of claim 2, wherein the external coil is enclosed within the thermal insulating base and the thermally conductive plastic.

4. The system of claim 3, wherein the thermal insulating base defines a first channel and the thermally conductive plastic defines a second channel, and wherein the external coil is sized to be received within the first channel and the second channel when sandwiched between the thermal insulating base and the thermally conductive plastic.

5. The system of claim 4, wherein the first channel is deeper than the second channel.

6. The system of claim 1, wherein the thermal insulating base is coated with rubber.

7. The system of claim 1, further including at least one temperature sensor disposed between the external coil and the thermally conductive plastic.

8. The system of claim 1, wherein the thermal insulating base comprises foam.

9. The system of claim 1, further including a garment alignment fabric layer coupled to the housing.

10. The system of claim 9, wherein the garment alignment fabric layer comprises polypropylene.

11. An external coil system for a transcutaneous energy transfer system (TETS), the system comprising:
 an external coil configured to transfer energy sufficient to power an implantable blood pump; and
 a housing comprising:
  a foam base, the external coil being partially disposed within the foam base; and
  a thermally conductive plastic, the external coil being partially disposed within the thermally conductive plastic, the thermally conductive plastic being coated with rubber; and
  a plurality of temperature sensors disposed within the housing.

12. The system of claim 11, wherein the external coil is sandwiched between the foam base and the thermally conductive plastic.

13. The system of claim 12, wherein the external coil is enclosed within the foam base and the thermally conductive plastic.

14. The system of claim 13, wherein the foam base defines a first channel and the thermally conductive plastic defines a second channel, and wherein the external coil is sized to be received within the first channel and the second channel when sandwiched between the foam base and the thermally conductive plastic.

15. The system of claim 14, wherein the first channel is deeper than the second channel.

16. The system of claim 11, wherein the foam base is coated with rubber.

17. The system of claim 11, wherein at least one temperature sensor of the plurality of temperature sensors is disposed between the external coil and the thermally conductive plastic.

18. The system of claim 11, further including a garment alignment fabric layer coupled to the foam base, the garment alignment fabric layer being configured to couple the housing to a garment.

19. The system of claim 18, wherein the garment alignment fabric layer comprises polypropylene.

20. An external coil system for a transcutaneous energy transfer system (TETS), the system comprising:
 an external coil configured to transfer energy sufficient to power an implantable blood pump;
 a housing comprising:
  a foam base coated with rubber and defining a first channel;
  a thermally conductive plastic defining a second channel, wherein the external coil is sized to be received within the first channel and the second channel when sandwiched between the foam base and the thermally conductive plastic; and
  a plurality of temperature sensors disposed within the housing on a surface of the external coil; and
 a garment alignment fabric layer coupled to the housing.

* * * * *